United States Patent
Yang et al.

(10) Patent No.: US 7,341,752 B2
(45) Date of Patent: Mar. 11, 2008

(54) ANTIBACTERIAL TREATMENT AND COMPOSITION

(75) Inventors: Wen-Chin Yang, Taichung County (TW); Shu-Lin Chang, Hsin-Chu (TW)

(73) Assignee: Academia Sinica, Taipei (TW)

( * ) Notice: Subject to any disclaimer, the term of this patent is extended or adjusted under 35 U.S.C. 154(b) by 162 days.

(21) Appl. No.: 11/215,765

(22) Filed: Aug. 30, 2005

(65) Prior Publication Data

US 2007/0048395 A1 Mar. 1, 2007

(51) Int. Cl.
*A61K 36/00* (2006.01)
*A61K 36/11* (2006.01)
*A01N 43/04* (2006.01)

(52) U.S. Cl. .................. 424/764; 424/725; 514/27

(58) Field of Classification Search .................. 424/725
See application file for complete search history.

(56) References Cited

U.S. PATENT DOCUMENTS 4,460,685 A    7/1984   Vilcek et al.
5,510,387 A    4/1996   Leonidov et al.
5,827,934 A *  10/1998  Villemez et al. ............ 530/409

OTHER PUBLICATIONS

Kaij-A-Lamb, Screening of in vitro antiviral activity from Brittany plants, specially from *Centaurea nigra*, J. Pharm. Belg. 1991,46,5, 325-326.*
Karrow et al. "Thalidomide modulation of the immune response in female B6C3F1 mice: a host resistance study". International Immunopharmacology 3:1447-1456, 2003.
Steinmuller et al. "Polysaccharaides isolated from plant cell cultures of *Echinacea purpurea* enhance the resistance of immunosuppressed mice against systematic infections with *Candida Albicans* and *Listeria Momocytogenes*". International Journal of Immunopharmacology 15(5):605-614, 1993.

* cited by examiner

*Primary Examiner*—Christopher R. Tate
*Assistant Examiner*—Randall Winston
(74) *Attorney, Agent, or Firm*—Occhiuti Rohlicek & Tsao LLP

(57) ABSTRACT

A method for treating a bacterial infection in a subject by administration of an effective amount of centaurein alone or in combination with a bacteriocide. Also described is a composition containing an effective combined amount of centaurein and a bacteriocide useful for treating a bacterial infection in a subject.

11 Claims, No Drawings

ANTIBACTERIAL TREATMENT AND COMPOSITION

BACKGROUND

Bacterial pathogens pose an ongoing threat to public health.

Indeed, bacterial infections are increasingly difficult to treat with conventional antibiotic therapies, due to the prevalence of antibiotic-resistant bacterial strains. For example, despite the fact that turberculosis used to be readily treatable, its causative agent *mycobacterium tuberculosis* infects almost one third of the human population. In fact, tuberculosis was declared a global emergency by the World Health Organization. Antibiotic-resistant strains of bacteria are also potential agents for bioterrorism.

There is an urgent need for new compositions and methods that can be used alone or in combination with antibiotic therapies to treat bacterial infections.

SUMMARY

The present invention is based on the unexpected finding that the compound centaurein can be used to inhibit a bacterial infection. Surprisingly, a combination of a suboptimal dose of a bacteriocide and centaurein is effective for reducing a bacterial infection.

Accordingly, one aspect of the invention is a method for treating a bacterial infection in a subject in need. The method includes administering to the subject an effective amount of centaurein (e.g., by injection). The method can be used to treat a bacterial infection caused by a bacterial strain that is antibiotic-resistant. A "bacterial infection" refers to entry and proliferation of a bacterium that is pathogenic to its host. The term "treating" includes both preventing or inhibiting the onset of a pathogenic bacterial infection (i.e., prophylaxis) and inhibiting or eliminating a pathogenic bacterial infection after its onset in a host.

Another aspect of the invention is a method for treating a bacterial infection by administering an effective combined amount of a bacteriocide (e.g., an antibiotic) and centaurein to a subject in need. The bacteriocide and centaurein can be administered separately or together. The term "bacteriocide" refers to a composition that can kill bacteria or inhibit their proliferation.

The two methods referred to above can be used to treat various bacterial infections caused by entry of a bacterium into a host cell. For example, the bacteria can be of the genus *Listeria, Brucella, Legionella, Francisella*, or *Mycobacterium*. Preferably, a subject is diagnosed as needing treatment for a bacterial infection or being at risk for a bacterial infection before being treated.

Yet another aspect of the invention is a composition containing centaurein, a bacteriocide, and a pharmaceutically acceptable carrier, which can be used to treat a bacterial infection. A combination of centaurein and a bacteriocide can also be used for the manufacture of a medicament for treating a bacterial infection in a subject.

Other features or advantages of the present invention will be apparent from the following detailed description, and also from the claims.

DETAILED DESCRIPTION

Described below are compositions and methods of this invention for treating a bacterial infection in a subject.

Centaurein is a flavonoid found in plants of the genus *Centaurea*. It can be isolated, e.g., from *Bidens pilosa* (see Example 1).

Centaurein can be incorporated into pharmaceutical compositions alone or in combination with a bacteriocide into pharmaceutical compositions for prophylactic or therapeutic use in a subject that has or is at risk of a pathogenic bacterial infection. For example, a pharmaceutical composition can include an effective amount of centaurein and a pharmaceutically acceptable carrier. Alternatively, a pharmaceutical composition can include an effective combined amount of centaurein and a bacteriocide. Centaurein can be provided "alone" as a pure compound or as a component of a centaurein-enriched composition (e.g., a plant extract). The term "effective amount" refers to the amount of an active composition that is required to confer a prophylactic or therapeutic effect on the treated subject. The term "effective combined amount" refers to the amount a combination of active compositions sufficient to confer a prophylactic or therapeutic effect on the treated subject, where the included amount of each active composition by itself would be insufficient to confer an adequate prophylactic or therapeutic effect or would cause an undesirable effect.

Effective doses will vary, as recognized by those skilled in the art, depending on the types of bacterial infections treated, the stage and severity of the infections, the general health and/or age of the subject, previous treatments, route of administration, excipient usage, and the possibility of co-usage with other prophylactic or therapeutic treatment. The combination of centaurein with a low dose of an antibiotic for treatment of a bacterial infection, rather than using a therapeutically equivalent high dose of an antibiotic by itself, reduces the risk of selection for antibiotic resistance in the infecting bacteria.

Bacteriocides that can be used in combination with centaurein include antibiotics, e.g., amoxicillin, ampicillin, augmentin, cephalosporin, doxycycline, erythromycin, gentamycin, nystatin, penicillin, tetracycline, vancomycin, and zithromycin.

Other bacteriocides that can be combined with centaurein include, e.g., the antibacterial compositions described in U.S. Pat. Nos. 6,734,161 and 6,849,713.

A bacterial infection can be treated in a subject by administering to the subject centaurein as the sole active composition or in combination with a bacteriocide (e.g., an antibiotic). If the bacterial infection is to be treated with a combination of centaurein and a bacteriocide, the two active compositions can be administered simultaneously (i.e., as a single formulation or as two separate formulations), or they can be administered at separate times.

The efficacy of the treatment of a subject for a bacterial infection can be evaluated by collecting a biological sample from the subject at various time points and quantifying the presence of the pathogenic bacteria by known methods (e.g., by a quantitative polymerase chain reaction assay for a gene sequence found in the pathogenic bacteria). A reduction in the number of pathogenic bacteria or their proliferation indicates successful treatment of the subject for the bacterial infection.

The active compositions can be administered parenterally, orally, nasally, rectally, topically, or buccally. The term "parenteral" as used herein refers to subcutaneous, intracutaneous, intravenous, intramuscular, intra-articular, intra-arterial, intrasynovial, intrasternal, intrathecal, or intralesional, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

An active composition can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active centaurein compound. Examples of other carriers include colloidal silicon oxide, magnesium stearate, cellulose, sodium lauryl sulfate, and D&C Yellow #10.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Isolation of Centaurein from *Bidens pilosa*

Whole *B. pilosa* plants (1.2 kg) were ground and extracted twice with nine liters of boiling water. The two resulting solutions were pooled and lyophilized, yielding 66.4 g of a crude extract that was then resuspended in one liter of water. The aqueous resuspended extract was then serially extracted with ethyl acetate (EA) and butanol (BuOH) (1 L×3 for each partitioning). The aqueous, EA, and BuOH fractions were lyophilized, yielding 0.8 g of EA extract, 9.3 g of BuOH extract, and 56.2 g of aqueous extract.

Analytical chromatography of the BuOH extract was performed on a RP-18 silica gel open column with a methanol/water gradient solvent system. Centaurein was found to be enriched in the fraction eluted with 50% methanol. Centaurein was further purified on a Luna 5μ C18(2) HPLC column (Phenomenex) using a Jasco HPLC system equipped with a PU-1580 pump and a UV-1575 UV/VIS detector. Centaurein was eluted from the column using 25% methylcyanide.

Centaurein was characterized with the following analytical methods: melting points were determined with a Yanagimoto micromelting point apparatus. Optical rotations were measured using a JASCO DIP-1000 digital polarimeter. Infrared spectra were recorded on a Perkin-Elmer 983G spectrophotometer. $^1$H and $^{13}$C NMR spectra were performed on a Varian Unity Plus 400 spectrometer. ESI-MS was performed on a ThermoFinnigan LCQ Advantage ion trap mass spectrometer.

EXAMPLE 2

Use of Centaurein to Prevent a Bacterial Infection in Mice

Six-to-eight week-old C57BL/6J mice were injected intraperitoneally with centaurein at a dose ranging from 0-20 μg per capita. After twenty four hours, the same mice were injected with pathogenic Listeria bacteria. A dose of 1-2×10$^6$ bacteria were introduced intraperitoneally (in a total volume of 0.2 ml) into each mouse. The cumulative survival rates of the mice were then determined. Ten days after the mice were injected with *Listeria*, all of the mice receiving the highest dose of centaurein (i.e., 20 μg) were still alive. In contrast, only 10% of the mice that were injected with *Listeria* and not treated with centaurein survived. Thus, centaurein protected the mice from a Listerial infection.

EXAMPLE 3

Treatment with Centaurein Alone or in Combination with an Antibiotic to Treat a Bacterial Infection in Mice Six-to-eight week-old C57BL/6J mice were injected intraperitoneally with *Listeria* as described in Example 2. After twelve hours, the mice were subjected to intraperitoneal injection of vehicle, ampicillin (5 μg), centaurein (20 μg), or a combination of ampicillin (5 μg) and centaurein (20 μg). After 5 days, no greater than 65% of the mice survived the infection after treatment with 5 μg of ampicillin or 20 μg of centaurein alone. In contrast, 100% of the mice survived the infection after treatment with a combination of 5 μg of ampicillin and 20 μg of centaurein. Thus, a combination of centaurein and an antibiotic is effective for treating a bacterial infection.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating a bacterial infection in a subject in need thereof, comprising administering to the subject an effective amount of centaurein, wherein the bacterial infection is caused by entry of a bacterium into a cell in the subject and, wherein the bacterium is of the genus *Listeria, Brucella, Legionella, Francisella*, or *Mycobacterium*.

2. The method of claim 1, further comprising diagnosing the subject as needing treatment for the bacterial infection prior to administering the centaurein.

3. The method of claim 1, wherein the bacterium is of the genus *Listeria*.

4. The method of claim 1, wherein the bacterial infection is caused by a bacterial strain that is antibiotic-resistant.

5. The method of claim 1, wherein the effective amount of centaurein is administered by injection.

6. A method for treating a bacterial infection in a subject in need thereof, comprising administering to the subject an effective combined amount of a bacteriocide and centaurein, wherein the bacterial infection is caused by entry of a bacterium into a cell in the subject and, wherein the bacterium is of the genus *Listeria, Brucella, Legionella, Francisella*, or *Mycobacterium*.

7. The method of claim 6, further comprising diagnosing the subject as needing treatment for a bacterial infection prior to the administration of the effective combined amount of a bacteriocide and centaurein.

8. The method of claim 6, wherein the bacteriocide is an antibiotic.

9. The method of claim 6, wherein the bacterium is of the genus *Listeria*.

10. The method of claim 6, wherein the effective combination is administered by injection.

11. The method of claim 6, wherein the antibiotic and the centaurein are administered separately.

* * * * *